United States Patent [19]

Sanderson et al.

[11] 3,970,701
[45] July 20, 1976

[54] LOWER ALKENALS

[75] Inventors: Anne Sanderson, Highlands; William L. Schreiber, Ocean, both of N.J.; Michel van Praac, Hilversum, Netherlands; Alan O. Pittet; William J. Evers, both of Atlantic Highlands, N.J.

[73] Assignee: International Flavors & Fragrances Inc., New York, N.Y.

[22] Filed: July 30, 1973

[21] Appl. No.: 383,578

[52] U.S. Cl. .......................... 260/601 R; 426/590; 426/803
[51] Int. Cl.² ........................................ C07C 47/20
[58] Field of Search .................. 260/601 R; 426/534

[56] References Cited
OTHER PUBLICATIONS

Wiemann et al., "Bull. Soc. Chim. de France", pp. 1760–1763 (1966).
Scharmueller et al., "Chem. Abstracts", vol. 71, Abstr: No. 122582c (1969).
Tiffeneau et al., Comptes Rend. 204, pp. 590–592 (1937).

*Primary Examiner*—Alton D. Rollins
*Assistant Examiner*—D. B. Springer
*Attorney, Agent, or Firm*—Arthur L. Liberman; Harold Haidt

[57] ABSTRACT

Novel lower 2-alkylidene-3-alkenals having the formula:

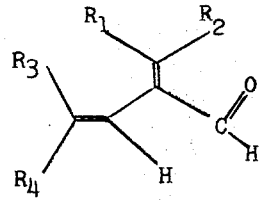

wherein one of $R_1$ and $R_2$ is hydrogen and the other is methyl, and one of $R_3$ and $R_4$ is hydrogen and the other is an alkyl group having two or four carbon atoms, such alkenals being useful in altering organoleptic properties of consumable materials.

1 Claim, No Drawings

LOWER ALKENALS

BACKGROUND OF THE INVENTION

The present invention provides novel alkylidene alkenals useful for altering the organoleptic properties of consumable materials such as foodstuffs, tobacco products, and perfumes.

U.S. Pat. No. 3,463,818 shows unsaturated aldehydes having various floral odors and processes for preparing such compounds. Japanese published application 72/43526 shows the synthesis of terpene derivatives having orange-like odors, and hexadienal derivatives are shown. Wiemann et al, Bul. Soc. Chem. de France *Memoires Presentes Soc. Chim.*, 1966, 1760, describe nuclear magnetic residence studies on some conjugated dienals, and a number of these compounds, including 2-ethylidene-3-pentenal are shown. 2-Propenyl-2-pentenal is mentioned in Chem. Abstracts 35, 6238.

West German published application 1,951,883 is said in *Chem. Abstracts* 75, 5246 to show preparation of dienals useful as perfumes. Tiffeneau et al, *Comptes Rend.* 204, 590 show the preparation of 2-alkylidene-3-butenal.

U.S. Pat. Nos. 3,272,873; 3,453,317; and 3,493,619 show processes for preparing unsaturated aldehydes or for treating such aldehydes. U.S. Pat. No. 3,520,936 shows production of an unsaturated aldehyde, and U.S. Patent 3,542,878 shows an aldol condensation using a tin catalyst.

Odiger et al Annalen 682 58; Corey et al, *J. Am. Chem. Soc.* 90, 6816; and Wittig et al, *Chem. Ber.* 94 676 show alkylidenation reactions utilizing phosphorus compounds. Goldberg et al shows selective reduction of unsaturated Schiff base systems in *J. Am. Chem. Soc.* 77, 1955.

THE INVENTION

The present invention provides novel 2-alkylidene-3-alkenals useful for altering the organoleptic properties of consumable materials. Briefly, the novel compounds are 2-alkylidene-3-alkenals having the formula:

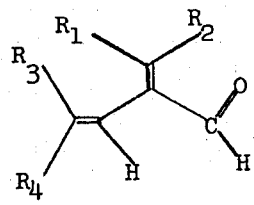

wherein one of $R_1$ and $R_2$ is hydrogen and the other is methyl, and one of $R_3$ and $R_4$ is hydrogen and the other is an alkyl group containing two or four carbon atoms.

Thus, the alkyl groups contemplated according to the present invention are lower alkyl groups. Preferably the alkyl groups represented by $R_3$ and $R_4$ are ethyl or isobutyl.

It will be understood from the present disclosure that several "cis-trans" isomers are possible as a result of the presence of substituents on the carbon atoms surrounding the carbon-carbon double bond of the alkenal chain as well as the alkylidene moiety and such isomers are contemplated herein. As an instance, a particularly preferred alkenal is trans-2-ethylidene-cis-3-hexenal, the compound according to the foregoing formula when $R_1$ is methyl and $R_3$ is ethyl. The structure of this compound can be written:

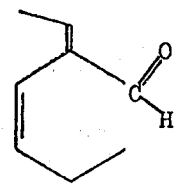

with the methyl group trans to the carbonyl.

The trans-2-ethylidene-cis-3-hexenal:

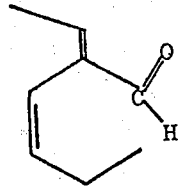

has a citrus, albedo-like character which ideally suits it for use in citrus flavors and particularly orange. In orange drink, it imparts a juice-like character and improves the sweetness. 2-Ethylidene-6-methyl-cis-3-heptenal (primarily trans-2-ethylidene-6-methyl-cis-3-heptenal):

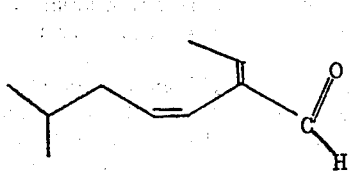

has a green, floral, slightly cucumber top fragrance note with a twig-like undertone particularly suiting it for use in fragrance compositions.

Trans-2-ethylidene-trans-3-hexenal,

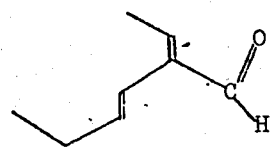

has an odor noticeably different from the trans-2-ethylidene-cis-3-hexenal material disclosed above, having more of a musty, harsher nuance.

Cis-2-ethylidene-cis-3-hexenal,

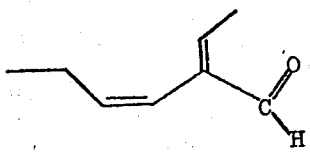

in admixture with trans-2-ethylidene-cis-3-hexenal and the diethyl acetal of cis-2-ethylidene-cis-3-hexenal in the following proportion:

| | |
|---|---|
| Cis-2-ethylidene-cis-3-hexenal | 70% |
| Trans-2-ethylidene-cis-3-hexenal | 20% |
| Diethyl acetal of cis-2-ethylidene-cis-3-hexenal | 10% | at 0.5 ppm imparts a "juicier" note to orange drink flavor. The taste has dominating fresh green notes with light, spicy backnotes. It has a delicate, green, twiggy, leafy, fruity, aroma note with a natural cinnamon note on dry-out.

The 2-alkylidene-3-alkenal derivatives and mixtures thereof according to the present invention can be used to alter, vary, fortify, modify, enhance, or otherwise improve the organoleptic properties, including flavor and/or aroma, of a wide variety of materials which are ingested, consumed, or otherwise organoleptically sensed. The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such 2-alkylidene-3-alkenal derivatives are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs include meats, gravies, soups, convenience foods malt and other alcholic or non-alcholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products include those designed or used for smoking such as in cigarette, cigar, and pipe tobacco, as well as products such as snuff, chewing tobacco, and the like.

When the 2-alkylidene alkenal derivatives according to this invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

The 2-alkylidene alkenal derivatives, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The alkenal compounds according to this invention can be incorporated with the carriers by conventional means such as spray-drying, drum-drying, and the like. Such carriers can also include materials for coacervating the alkylidene alkenal derivatives (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

When the derivatives are used to treat tobacco products for example, the additive can be applied in a suitable manner, as by spraying, dipping, or otherwise. They can be applied during the "casing" or final spray treatment of the tobacco, or they can be applied at some earlier stage of curing or preparation. The quantity of alkylidene alkenal derivatives or mixtures thereof utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff, tobacco product, or other consumable product; the amount and type of flavor initially present in the product; the further process or treatment steps to which the product will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff, tobacco, or other consumable material.

It is accordingly preferred that the ultimate compositions contain from about 0.02 parts per million (ppm) to about 150 ppm of 2-alkylidene alkenal derivative or derivatives. More particularly, in food compositions it is desirable to use from about 0.05 ppm for enhancing flavors and in certain preferred embodiments of the invention, from about 0.2 to 50 ppm of the derivatives are included to add positive flavors to the finished product. On the other hand, tobacco compositions can contain as little as 0.5 ppm and as much as 250 ppm depending upon whether a cigarette tobacco, a pipe tobacco, a cigar tobacco, a chewing tobacco, or snuff is being prepared. All parts, proportions, percentages, and ratios herein are by weight unless otherwise indicated.

The amount of 2-alkylidene alkenal material or materials to be utilized in flavoring compositions can be varied over a wide range depending upon the particular quality to be added to the foodstuff, tobacco, or other consumable material. Thus, amounts of one or more derivatives according to the present invention from about 2 ppm up to 80 or 90 percent can be incorporated in such compositions. It is generally found to be desirable to include from about 10 ppm to about 0.1 percent of the derivatives in such compositions.

The 2-alkylidene alkenal derivatives of this invention are also useful individually or in admixture as fragrances. They can be used to contribute various fruity, woody, or floral fragrances. As olfactory agents, the derivatives of this invention can be formulated into or used as components of a "perfume composition".

A perfume composition is composed of a small but effective amount of an 2-alkylidene-3-alkenal derivative according to this invention and an auxiliary perfume ingredient, including, for example, alcohols, aldehydes, ketones, nitriles, esters, and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation, and (d) top-notes which are usually low-boiling fresh-smelling materials.

It will thus be apparent that the derivatives according to the present invention can be utilized to alter the sensory properties, particularly organoleptic properties such as flavor and/or fragrance of a wide variety of consumable materials.

The novel 2-alkylidene alkenals of the present invention can readily be prepared by a number of reaction routes, as will be apparent to those skilled in the art from the present disclosure. Thus, they can be prepared by reacting an alkyl metallo acetylide with a dialkoxyacetonitrile to form an imine salt, hydrolyzing the imine salt to form 1,1-dialkoxy-3-alkyn-2-one, treating the 1,1-dialkoxy-3-alkyne-2-one with an alkylidene triphenyl phosphorane, hydrolyzing the 1,1-dialkoxy-2-alkylidene-3-alkyne so formed in acidic aqueous solution to provide 2-alkylidene-3-alkynal, and reducing the triple bond to a double bond as by hydrogenation to obtain the novel 2-alkylidene-3-alkenal.

It is significant that hydrogenation of the 1,1-dialkoxy-3-alkyne-2-one will yield, primarily, the isomer 1,1-dialkoxy-cis-3-alkene-2-one which is then isomerized to the 1,1-dialkoxy-trans-3-alkene-2-one using an appropriate cis-trans isomerization reagent such as a mixture of acetic acid and sodium iodide or potassium iodide (Preferred concentration range of alkali metal iodide in acetic acid, from 0.5% up to 2% by weight). It should further be noted that hydrolysis of the 1,1-dialkoxy-2-alkylidene-trans-3-alkenal produced as the result of reaction of the tri-substituted alkylidene phosphorane with the 1,1-dialkoxy-3-trans-alkene-2-one will yield a mixture of cis-2-alkylidene-trans-3-alkenal and trans-2-alkylidene-trans-3-alkenal. The cis-2-alkylidene-trans-3-alkenal in the mixture may then be specifically isomerized to the trans-2-alkylidene-trans-3-alkenal (thus creating a material containing only the one isomer, to wit: trans-2-alkylidene-trans-3-alkenal) by means of an appropriate cis-trans isomerization agent such as a mixture of acetic acid and an alkali metal iodide such as sodium iodide or potassium iodide.

Alternatively, the compounds described herein can be produced by a process comprising the steps of: (1) reacting an aliphatic α,β-unsaturated aldehyde with an halogen to provide the corresponding α-halo aldehyde derivative; (2) either (i) reacting the said α-halo aldehyde derivative with an alkyl magnesium halide (Grignard reagent) hydrolyzing the resulting product to form a hydroxyhaloalkene and dehydrating the resulting hydroxyhaloalkene to form a trans halo alkadiene or (ii) reacting the said α-halo aldehyde derivative with a trisubstituted alkylidene phosphorane or an alkylidene phosphorous triamide to provide a mixture of cis and trans halo alkadienes having structures:

(3) either (i) treating either the mixture of said halo alkadiene isomers or said trans halo alkadiene with a metal such as magnesium thereby forming an organometallic reagent and reacting the said organometallic reagent so formed with a trialkyl orthoformate to yield an acetal which is then hydrolyzed with acid to yield the desired alkylidene-trans-alkenal or (ii) reacting the mixture of halo alkadiene isomers with an alkyl lithium to form a lithioalkadiene (mixture of isomers) and then reacting said organometallic reagent with a dialkyl formamide or an aryl alkyl formamide followed by acid hydrolysis thus forming a mixture of 2-alkylidene-cis-3-alkenal and alkylidene-trans-3-alkenal or (iii) physically separating the cis halo alkadiene from the trans halo alkadiene and then reacting each isomer independently with an alkyl lithium to form lithio alkadienes and then reacting each of said lithio alkadienes with a dialkyl formamide or an aryl alkyl formamide followed by acid hydrolysis forming, separately, an alkylidene-trans-alkenal and an alkylidene-cis-alkenal.

In these reactions, the various alkyl and alkylidene substituents are chosen to provide the desired final compounds. The cis-trans isomer ratios are controlled by suitable reaction conditions and/or separation techniques.

The intermediate and/or final products obtained can be purified or isolated by conventional purification after appropriate washing, neutralizing and/or drying as appropriate. Thus, such products can be purified and/or isolated by distillation, steam distillation, vacuum distillation, extraction, preparative chromatographic techniques, and the like.

The following examples are given to illustrate embodiments of the invention as it is presently preferred to practice it. It will be understood that these examples are illustrative, and the invention is not to be considered as restricted thereto except as indicated in the appended claims.

EXAMPLE I

PREPARATION OF 2-ETHYLIDENE-CIS-3-HEXENAL i. Preparation of 1,1-Dimethoxy-3-hexyne-2-one An ether solution of ethylmagnesium bromide is prepared from 7.3 g magnesium turnings and 32.7 g ethyl bromide. About 20 g ethyl acetylene is admitted as a gas under a dry ice condenser and the mixture is refluxed for two hours until gas evolution ceases. The mixture is then cooled below 0°, and 30.3 g of dimethoxy acetonitrile is added in ether solution.

The mixture is allowed to come to room temperature and stirred for 2 hours, during which time the lower layer of the two-phase mixture becomes almost solid. The mixture is again cooled and treated with 16 ml sulfuric acid diluted with 300 ml water. The layers are separated and the organic layer is washed successively with saturated aqueous sodium chloride solution and saturated aqueous sodium bicarbonate solution and then dried over 4A molecular sieves. Thorough removal of solvent gives 35.3 g of yellow oil – 99% pure by GLC (gas-liquid phase chromatography).

ii. Preparation of 2-Ethylidene-3-hexynal Dimethyl Acetal

Ethyltriphenylphosphonium bromide (24.8 g) is stirred with 100 ml benzene, and 40 ml (1.6 N) butyl lithium in hexane is added over about one-half hour with a water bath used to take up the slight heat of reaction. The mixture (bright orange) is stirred at room temperature for 0.75 hour, and 10.0 g of the 1,1-dimethoxy-3-hexyne-2-one is added dropwise in one-half hour.

After an additional 15 minutes at 40° (water bath) the mixture is filtered and evaporated at reduced pressure through a fractionation column. The residue is dissolved in isopentane, filtered, and again evaporated to provide 4.3 g of a yellow orange oil. Gas chromatographic, mass spectral and nuclear magnetic resource (NMR) data indicate that the major peaks are isomers of the desired structures:

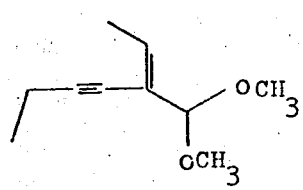

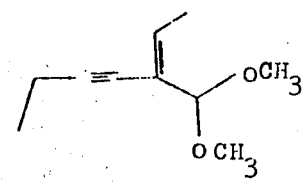

iii. Preparation of 2-Ethylidene-3-hexynal

The acetal isomers so produced are dissolved in 50 ml ether and stirred for 1½ hours with 25 ml water containing 2.5 g oxalic acid (room temperature). The layers are separated and washed successively with saturated aqueous sodium carbonate solution and brine, and evaporated at atmospheric pressure through a Vigreux column. After removal of the last traces of solvent in vacuo there remains 3.0 g of reddish oil. GC-MS and NMR confirm that the major product is 2-ethylidene-3-hexynal.

iv. Preparation of 2-Ethylidene-cis-3-hexenal

The 2-ethylidene-3-hexynal so prepared (2.5 g) is dissolved in 20 ml hexane and a small amount of solid is removed by filtration through a pad of neutral alumina. The solution is then mixed with 0.25 g Lindlar catalyst (palladium on calcium carbonate poisoned with lead acetate) and stirred under hydrogen gas at about one atmosphere pressure for 6½ hours. The resulting mixture is filtered and the solvent removed through a Vigreux column. The major component, isolated from a Carbowax(polyethylene glycol)-packed GLC column is demonstrated by IR, NMR, and MS spectral data to be

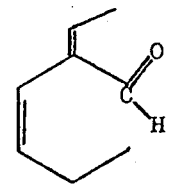

The other 2-alkylidene-3-alkenals according to the present invention are similarly prepared.

In the following NMR spectra, the shifts in ppm relative to a tetramethylsilane standard are measured in carbon tetrachloride at 100 MHz. The 2-ethylidene-cis-3-hexenal produced in Example I shows the following:

| Shift | No. of Protons | Peak | Assignment |
|-------|----------------|------|------------|
| 0.92 | 3 | Triplet | $CH_3—CH_2—$ |
| 1.88 | | Doublet | $CH_3—C=C—C=O$ |
| 1.92–1.70 | 5 | Multiplet | $CH_3—CH_2—C=C—$ |
| 5.75 | 2 | Multiplet | Olefinic protons |
| 6.61 | 1 | Quartet | $CH_3—\underline{CH}=C—C=O$ |
| 9.41 | 1 | Singlet | Formyl proton |

EXAMPLE II

Ten liters of orange juice, concentrated as an aqueous essence by Libby, McNeil & Libby Corp. of Ocala, Florida, is extracted with diethyl ether in a Quickfit Multi-purpose Extractor. After drying the ether extract with anhydrous megnesium sulfate, the extract is concentrated in a Kuderna-Danish apparatus and analyzed by GLC and GLC/MS analysis using an F&M 5750 Chromatograph equipped with a flame ionization detector operating under the following conditions:

| | |
|---|---|
| Carrier gas: | Helium |
| Flow rate: | 40 ml/min. |
| Recorder speed: | 0.25 inches/min. |
| Detector: | F.I.D. at 250°C |
| Column: | 10' × 1/8" O.D. 25% Carbowax 20 M on 60/80 mesh DMCS-treated Chromosorb WAW |
| Program rate: | 50°–225° C at 2°/min. |

The GLC/MS system used has the following components:

| | |
|---|---|
| GLC: | Aerograph 1520 |
| Detector: | F.I.D. at 200°C |
| Column: | Support-coated Carbowax 20 M, 0.02" I.D. |
| Program rate: | Ambient to 175°C at 2°/min. |

-continued

| | |
|---|---|
| Effluent split: | 6:1 to MS |
| MS: | Hitachi RMU 6E equipped with a Watson-Biemann separator in the MS oven, allowing for rapid-scan spectra of compounds separated by chromatography. |

Those compounds giving only weak mass spectra are trapped out on a semi-preparative scale under the following conditions:

| | |
|---|---|
| GLC: | F & M 700 |
| Detector: | T.C. at 250°C |
| Carrier gas: | Helium |
| Flow rate: | 80 ml/min. |
| Column: | 8' × 1/4" O.D. 25% Carbowax 20 M on 60/80 mesh Chromosorb WAW. |
| Program rate: | 75°–225° C at 2°/min. |

Compounds trapped from orange juice extract that could not be identified by GLC/MS are submitted to NMR and IR for further structural analysis.

A particular compound obtained is an unsaturated aldehyde of molecular weight 124. High resolution MS yields the elemental formula $C_8H_{10}O$ and from UV (ultraviolet) spectral analysis the compound is shown to be a monosubstituted $\alpha,\beta$-unsaturated aldehyde. An NMR-spectrum is recorded and these data, together with the complete mass spectrum, show that the compound is 2-ethylidene-cis-3-hexenal (substantially trans-2-ethylidene-cis-3-hexenal)

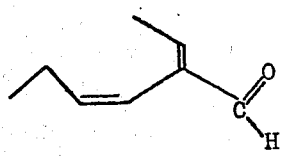

Mass spectral analysis (low resolution) shows the principal m/e ratios: 39, 41, 109, 81, 67, 95 . . . 124 (Parent Peak).

The NMR data show ($\tau$ in ppm): (solvent-CCl$_4$):

| $\tau$ | J (cps) | No. of protons | Peak | Assignment |
|---|---|---|---|---|
| 9.04 | 7 | 3 | Triplet | CH$_3$—CH$_2$— |
| 8.12 | 6 | 3 | Doublet | CH$_3$—CH=C—CHO |
| 4.34 | 4 | 2 | Doublet | cis C$_2$H$_5$—CH=CH— |
| | | | | C |
| 3.56 | 6 | 1 | Quartet | —CH=C=CHO |
| | | | | C |
| 0.72 | — | 1 | Singlet | —CH—C—CHO |

At 1.5 ppm the 2-ethylidene-3-hexenal obtained has a pleasant fresh green aroma with a fatty waxy character. At 15 ppm in water the hexenal derivative has a fresh green, waxy character. In a 12% sucrose solution containing 0.1% citric acid at a level of 1.5 ppm it has a fresh green, waxy character reminiscent of citrus fruit rind. At 33 ppm in water solution it has a clean green, pleasant and intense leafy odor. The taste is reminiscent of the white pulpy material, or albedo, of the orange. The odor and taste at 33 ppm of the 2-ethylidene-3-hexenal impart the aromatic characteristics evident in citrus juices.

EXAMPLE III

Preparation of 2-Ethylidene-6-methyl-cis-3-heptenal

A solution of 5.40 g of isobutylacetylene in 50 ml of diethyl ether is treated with 30 ml of 2.2 N n-butyllithium in hexane at −20°C, and after several minutes the resulting solution is treated with 8.50 g of diethoxyacetonitrile and then warmed slowly to room temperature. After about 1.5 hours the dark mixture is cooled and brought to a pH of about 2 with ten percent sulfuric acid.

The layers are then separated and the organic layer is washed successively with water and saturated aqueous sodium bicarbonate solution and then dried over sodium sulfate. Evaporation of the solvent provides 4.6 g of a dark oil, shown by IR and NMR to contain 1,1-diethoxy-6-methyl-3-heptyn-2-one.

A solution of ethylidenetriphenylphosphorane is prepared by admixing 17.0 g of ethyltriphenylphosphonium bromide with 20 ml of 2.3 N phenyllithium in a 70:30 benzene: ether vehicle. This is added to the heptynone, with the temperature being held below 30°C with cooling.

A few minutes after the addition is completed, the mixture is partitioned between water and ether phases. The layers are separated, and the organic phase is dried over sodium sulfate and evaporated. The residue is dissolved in hexane and filtered to remove triphenylphosphine oxide. After evaporation of the hexane, the 10.4 g of crude acetal obtained is hydrolyzed to the acetylenic aldehyde in 30 percent aqueous acetic acid.

The crude aldehyde is isolated by partitioning between water and ether; the ether layer is washed successively with water and saturated aqueous sodium carbonate and dried over sodium sulfate; and the solvent is evaporated. The residue is hydrogenated in hexane solution over 1.0 g of Lindlar catalyst (5 percent palladium on calcium carbonate poisoned with lead acetate) at a pressure of about four atmospheres.

The mixture is filtered and the solvent is evaporated to provide 3.8 g of dark oil from which the 2-ethylidene-6-methyl-cis-3-heptenal is isolated by preparative GLC.

The NMR spectrum of the material shows:

| Shift | No. of Protons | Peak | Assignment |
|---|---|---|---|
| 1.00 | 6 | Doublet | —HC(CH$_3$)$_2$ |
| 1.70 | 2 | Quartet | =C—CH$_2$ |
| 1.88 | 3 | Doublet | —CO—C=C—CH$_3$ |
| 5.80 | 2 | Multiplet | definic protons |
| 6.70 | 1 | Quartet | CH$_3$—CH=C—C=O |
| 9.37 | 1 | Singlet | Formyl proton |

The material

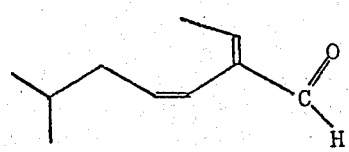

has a green, floral, violet slightly cucumber fragrance.

EXAMPLE IV

Orange Flavor Formulation

An orange flavor formulation is prepared by admixing:

| Ingredients | Parts |
|---|---|
| Natural orange oil | 13.00 |
| Acetaldehyde | 1.50 |
| Ethyl acetate | 0.10 |
| Ethyl butyrate | 0.50 |
| Propanal | 0.10 |
| trans-2-Hexenal | 0.10 |
| Ethyl alcohol (95%) | 60.00 |
| Fusel oil | 0.05 |
| Propylene glycol | 24.65 |

This is denominated Flavor "A". A second formulation, Flavor "B" is prepared by adding trans-2-ethylidene-cis-3-hexenal (one percent in ethanol) to a portion of Flavor "A" in the ratio of 2 parts to 100 parts of Flavor "A".

Each of Flavors "A" and "B" is added in the amount of two ounces per gallon of 32° Baume sugar syrup to produce a syrup for combination with water to form a drink. The beverage prepared using Flavor "A" is a passable orange beverage of good character, flavor and intensity.

The beverage prepared using Flavor "B" has a much improved flavor. The improvement contributed by the ethylidenehexenal is due to:

1. a greater degree of the natural character of freshly squeezed orange juice
2. an increase in the pulplike notes
3. greater orange juice flavor depth.

EXAMPLE V

Preparation of 1,1-Dimethoxy-cis-3-hexene-2-one

Six grams of the 1,1-dimethoxy-3-hexyne-2-one (of Example I) is stirred under hydrogen gas at one atmosphere in 40 ml hexane containing 0.6 g Lindlar catalyst (palladium on calcium carbonate poisoned with lead acetate) and 4.0 g quinoline. The reaction is terminated when one percent of the starting material (1,1-dimethoxy-3-hexyne-2-one) remains.

The mixture is filtered and the quinoline washed out with dilute aqueous hydrochloric acid. The organic layer is washed with saturated aqueous sodium bicarbonate and then brine; the solvent is evaporated. GLC and NMR of the crude material shows the product is substantially 1,1-dimethoxy-cis-3-hexene-2-one having the structure:

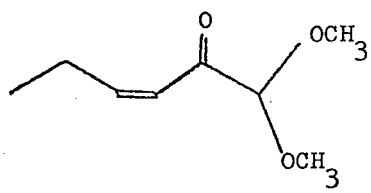

EXAMPLE VI

Preparation of 1,1-Dimethoxy-trans-3-hexene-2-one

The crude product produced in Example V is dissolved in 6 ml of acetic acid with 0.1 g of sodium iodide. By GLC on Carbowax(polyethylene glycol) it is clear that the 1,1-dimethoxy-cis-3-hexene-2-one is converted to a new material of later retention time. After one-half hour less than 5 percent of "cis" material remains.

The material is isolated by partitioning between water and ether, washing the ether layer successively with aqueous sodium bicarbonate and brine and then drying over 4A molecular sieves. Evaporation of the solvent provides 5.0 g of yellow oil. NMR and GLC indicate essentially all trans material having the structure:

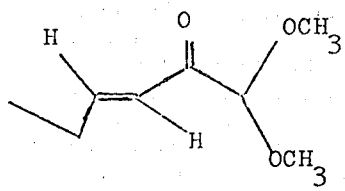

EXAMPLE VII

Ethyltriphenylphosphonium bromide (3.71 g) and 6.3 ml of 1.6 N n-butyl lithium are mixed in ether solution and 1.58 g of the 1,1-dimethoxy-trans-3-hexene-2-one of Example VI is added, while keeping the internal temperature below 30°C. After a few minutes the mixture is filtered and the solvent evaporated. A small amount of solid is present so the residue is dissolved in isopentane, filtered, and again evaporated to give 1.10 g of a yellow-orange oil.

GLC and NMR indicate the presence of two acetals of 2-ethylidene-trans-3-hexenal: cis and trans isomers at the ethylidene group namely: cis-2-ethylidene-trans-3-hexenal dimethyl acetal and trans-2-ethylidene-trans-3-hexenal dimethyl acetal. The acetal material is dissolved in 2 ml water and 3 ml acetic acid with a small amount of sodium iodide isomerization reagent. After a few minutes GLC shows complete hydrolysis. (In the absence of sodium iodide a mixture of cis and trans ethylidene isomers of the aldehydes is obtained).

The product is isolated by partitioning between water and ether. The organic layer is washed successively with water, aqueous sodium bicarbonate, and aqueous sodium chloride and finally evaporated to give 0.70 g of an orange oil. The major peak (80%), isolated by preparative GLC is trans-2-ethylidene-trans-3-hexenal having the structure:

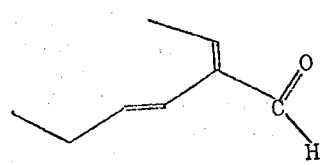

EXAMPLE VIII

Preparation of (Z)-2-Ethylidene-(Z)-3-hexenal (or cis-2-ethylidene-cis-3-hexenal)

A slurry of 4.20 g ethyltriphenylphosphoniumiodide in 30 ml ether is mixed with 4.3 ml 2.3N phenyllithium in benzene: ether to provide a deep orange solution. 1,1-Dimethoxy-3-hexyne-2-one as obtained in Example I (1.56 g) is added, keeping the temperature below 30°, and the resulting mixture is stirred one hour. Water and more ether are added, the mixture is filtered, the layers separated, and the organic layer washed with brine and then evaporated.

The residue is dissolved in isopentane, filtered, and evaporated to give 2.0 g of orange-colored oil. The crude product is hydrogenated at about one atmosphere pressure in 10 ml pyridine over 0.2 g palladium on barium sulfate and the material is re-isolated by partitioning between ether and water. The organic layer is washed several times with water and then saturated aqueous sodium chloride.

After removal of solvent there is a red-orange oil which contains some pyridine. The major product is isolated by preparative GLC. The trapped material (140 mg.) is hydrolyzed by stirring it in ether solution with 5 percent sulfuric acid. After 1½ hours at room temperature the mixture is worked up by separating the layers, washing the ether layer with aqueous sodium bicarbonate followed by saturated aqueous sodium chloride and evaporating through a Vigreux column to give 110 mg of a very pale green oil with a fresh "green" aroma.

By GLC it is found to contain 10 percent of the acetal, and by NMR, to contain 20 percent of the stable isomer. The major product is the cis-2-ethylidene-cis-3-hexenal isomer with the structure:

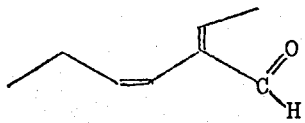

EXAMPLE IX

Tobacco Flavor

Two tobacco flavor formulations are prepared by admixing:

Formula A

| Ingredients | Parts |
| --- | --- |
| Pyroligneous acid | 10.00 |
| Solid extract cornsilk | 18.00 |
| Solid extract foenugreek | 3.50 |
| Vanillin | 0.15 |
| Cyclotene | 0.05 |
| 2-Ethyl-3-methylpyrazine | 0.10 |
| Methyl heptynyl carbonate | 0.05 |
| Eugenol | 0.10 |
| Trans-2-ethylidene-trans-3-hexenal (Produced by Example VII) | 1.00 |
| Propylene Glycol | 67.05 |

Formula B

| Ingredients | Parts |
| --- | --- |
| 2-Ethyl-3-methylpyrazine | 0.10 |
| 2-Methylvaleric acid | 1.00 |
| Methyl heptynyl carbonate | 0.25 |
| Pyroligneous acid | 10.00 |
| Trans-2-Ethylidene-cis-3-hexenal (Produced by Example I) | 1.00 |
| Vanillin | 0.02 |
| Solid extract foenugreek | 2.50 |
| Glycerine | 16.75 |
| Water | 20.00 |
| Solid extract cornsilk | 15.00 |
| Propylene glycol | 33.38 |

Both Formulas "A" and "B" are useful in tobacco as flavor enhancers. They enhance the sweet, maple, nut-like character and enhance the natural smell of the tobacco. The tobacco blend on which the flavors are used contains:

| Ingredient | Amount |
| --- | --- |
| Virginia tobacco | 28% |
| Burley | 48% |
| Remaining tobaccos (Oriental, Turkish, stems, reconstituted tobacco) | 24% |

EXAMPLE X

Perfume Formulation

A perfume formulation is prepared by admixing:

| Ingredients | Parts |
| --- | --- |
| Linalool | 30 |
| Linalyl acetate | 10 |
| Terpineol coeur | 5 |
| Nerol coeur | 10 |
| Terpinyl acetate | 2 |
| Geranyl acetate | 2 |
| Neryl acetate | 2 |
| Methyl anthranilate | 1 |
| Citral | 10 |
| n-Decyl alcohol | 1 |
| n-Dodecyl alcohol | 5 |
| n-Dodecanal | 15 |
| n-Decanal | 30 |
| n-Nonanol | 3 |
| n-Nonanal | 5 |
| n-Decyl acetate | 5 |
| n-Dodecyl acetate | 3 |
| Trans-2-Ethylidene-cis-3-hexenal (Produced by Example I) | 5 |

The ethylidenehexenal imparts a natural, tart, orange character to this terpeneless orange perfume formulation.

EXAMPLE XI

Strawberry Flavor Formulation

A strawberry flavor concentrate is prepared by admixing:

| Ingredient | Percent |
| --- | --- |
| Napthyl ethyl ether | 0.96 |
| Ethyl methyl phenyl glycidate | 2.88 |
| Vanillin | 2.66 |
| 2-Methyl-2-pentenoic acid | 3.90 |
| Ethyl acetate | 9.58 |
| Isoamyl butyrate | 12.25 |
| Ethyl butyrate | 26.20 |
| Isoamyl butyrate | 40.57 |
| 1-(Prop-1'-enyl)-3,4,5-trimethoxybenzene | 0.50 |
| trans-2-ethylidene-cis-3-hexenal | 0.50 |

| Ingredient | Percent |
|---|---|
| (Produced by Example 1) | |

The concentrate so prepared is dissolved in four times its volume of propylene glycol and the mixture is added to a simple syrup at the rate of 8 ounces per gallon of syrup.

The syrup is acidified by the addition of 1.5 ounces of 50% aqueous citric acid solution to each gallon of syrup. A carbonated beverage is prepared by mixing one ounce of the flavored acidified syrup with five ounces of carbonated water. The beverage so prepared has an excellent fresh strawberry flavor and is found to be markedly superior to a beverage prepared in the same manner but without the trans-2-ethylidene-cis-3-hexenal. The beverage prepared without the trans-2-ethylidene-cis-3-hexenal is found to be lacking in fresh green flavor notes present in natural strawberry flavor and aroma. Such fresh green notes are supplied by the trans-2-ethylidene-cis-3-hexenal.

Similar good results can be obtained in altering the organoleptic properties of consumable materials with the other 2-alkylidene-3-alkenals of the invention, such as isomers of 2-ethylidene-6-methyl-3-heptenal, and the like. The various isomers do exhibit somewhat different organoleptic properties, as will be understood from the present disclosure.

What is claimed is:

1. A composition of matter consisting essentially of trans-2-ethylidene-cis-3-hexenal having the formula:

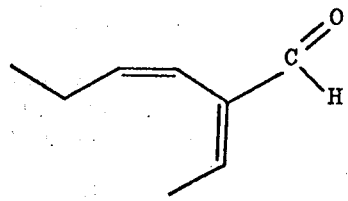

* * * * *

UNITED STATES PATENT AND TRADEMARK OFFICE
CERTIFICATE OF CORRECTION

PATENT NO. : 3,970,701

DATED : July 20, 1976

INVENTOR(S) : Anne Sanderson, et al

It is certified that error appears in the above-identified patent and that said Letters Patent are hereby corrected as shown below:

Cover page, [75], line 3, "Michel van Praac" should read --- Michel van Praag ---.

Signed and Sealed this

Twenty-sixth Day of October 1976

[SEAL]

Attest:

RUTH C. MASON
*Attesting Officer*

C. MARSHALL DANN
*Commissioner of Patents and Trademarks*